United States Patent
Ishikawa et al.

(10) Patent No.: US 9,988,396 B2
(45) Date of Patent: Jun. 5, 2018

(54) OXAZIRIDINE COMPOUND AND PRODUCTION METHOD THEREOF

(71) Applicant: SEED RESEARCH INSTITUTE CO., LTD., Kunigami-gun, Okinawa (JP)

(72) Inventors: Teruhiko Ishikawa, Okayama (JP); Morita Iwami, Okinawa (JP)

(73) Assignee: SEED RESEARCH INSTITUTE CO., LTD., Kunigami (JP)

( * ) Notice: Subject to any disclaimer, the term of this patent is extended or adjusted under 35 U.S.C. 154(b) by 0 days. days.

(21) Appl. No.: 15/416,869

(22) Filed: Jan. 26, 2017

(65) Prior Publication Data
US 2017/0327513 A1     Nov. 16, 2017

(30) Foreign Application Priority Data
May 11, 2016   (JP) ................. 2016-095265

(51) Int. Cl.
*C07D 491/02*     (2006.01)
*C07D 498/04*     (2006.01)
*C07D 491/044*    (2006.01)

(52) U.S. Cl.
CPC ....... *C07D 498/04* (2013.01); *C07D 491/044* (2013.01)

(58) Field of Classification Search
CPC .......................... C07D 498/04; C07D 491/044
USPC ....................................................... 546/115
See application file for complete search history.

(56) References Cited

PUBLICATIONS

Black et al, 13C NMR spectra of 1-Pyrroline 1-Oxides, 2H-Pyrrole 1-Oxides and Related Compounds, Magnetic Resonance in Chemistry, 1991, vol. 29, p. 1114-1118.*
Riviere et al, Interactions Des Complexes Du Chrome Ou Du Tungstene A Ligande Germylene Avec Des Dipoles 1,3(Nitrones, Oxaziridines), Journal of Organometallic Chemistry, 1986, 307, p. 205-218(two pages of abstract ).*
Black et al, Doppelte Ringoffnung bicyclischer Oxaziridine zu N-(3-Oxopropyl)amiden mit Eisen(II)-sulfat, Angewandte Chemie, 1981, 93(8),703-704.*
Bapat et al, Nitrones and oxaziridines. XII. Vinylogous hydroxamic acid structures of thereduction products from gamma-nitro(o-and p-hydroxyphneyl)ketone, Australian Journal of Chemistry, 1974, 27(7), 1591-1595, two pages of abstract.*
Riviere et al, Reactions of germylene chromium or tungsten complexes with 1,3-dipoles(nitrones, oxaziridines), Journal of Organometallic Chemistry, 1986, 307, p. 205-218(two pages of abstract ).*
Parello et al, Oxaziranes. Method for preparing nitrogen heterocycles by photolysis of an oxazirane. Preliminary results, Sciences Chimiques, 1971, 273(17), 1097-100, abstract page.*

* cited by examiner

*Primary Examiner* — Taylor V Oh
(74) *Attorney, Agent, or Firm* — Leydig, Voit & Mayer, Ltd.

(57) ABSTRACT

Provided are an oxaziridine compound showing an antifungal activity and cytotoxicity and expected as a new antifungal agent or anticancer agent, and a production method thereof.
A compound represented by the formula 1:

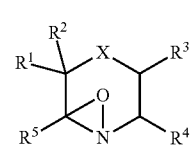

wherein
X is a single bond, —C(H)($R^6$)— or —C(H)($R^7$)—C(H)($R^8$)—; and
$R^1$-$R^8$ are each independently a hydrogen atom, an optionally substituted hydrocarbon group or an optionally substituted heterocyclic group,
or a salt thereof.

10 Claims, No Drawings

OXAZIRIDINE COMPOUND AND PRODUCTION METHOD THEREOF

TECHNICAL FIELD OF THE INVENTION

The present invention relates to an oxaziridine compound and a production method thereof.

BACKGROUND OF THE INVENTION

In recent years, along with an increase in elderly people, progress of advanced medicine, immunodeficiency of late stage cancer patients and the like, infections with fungi have been increasing. These infections provide serious effects, often causing death. Since there are not many kinds of existing antifungal agents, and their toxicity is high, the mother nucleus of a new antifungal agent, which is different from that of conventional medicaments, has been desired. In addition, since the use of antifungal agents causes increased emergence of resistant bacteria, the development of a new medicament has been earnestly desired. While candin-based antifungal agents show low toxicity, since the molecular weight thereof is large, reactivity with serum poses problems. Azole-based antifungal agents have a problem in that administration at a high concentration is difficult in view of the toxicity thereof. Therefore, an effective, low-molecular-weight compound showing low reactivity with serum and low toxicity has been strongly desired.

Conventionally, in search of a pharmaceutical product seed compound from microbial metabolites, terrestrial separation sources have been mainly harvested and subjected to microorganism separation. The microbial metabolites found to date include penicillin and adriamycin, and a number of antibiotics and anticancer agents were found and utilized as therapeutic drugs for infection, cancer and the like. However, due to the continuous search over a long term, microbial metabolites obtained from the land areas are mostly known compounds, and a secondary metabolite to be a candidate for a novel medicament is extremely difficult to obtain. Consequently, the development of a novel medicament by natural substance drug discovery corporations was rapidly reduced. To overcome the situation, screening using a chemical library (natural substance and synthesized compound) has been conducted on a global scale. Unexpectedly, however, a promising novel medicament candidate compound was not obtained from the chemical library. Under such circumstances, it is extremely difficult to obtain a new medicament candidate compound.

In view of the aforementioned current situation in the search of a novel medicament candidate compound, the marine microorganism resources have drawing attention. Marine microorganism resources have been scarcely utilized, and have a high possibility of affording a novel secondary metabolite.

Recently, a new compound represented by the following formula:

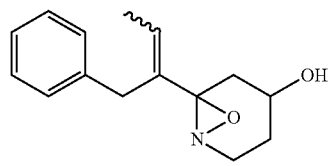

which was found from a microorganism collected from the seabed sand around the Kakeroma island of Kagoshima Prefecture, Amami Islands, was named "Kakeromycin". The "kakeromycin" shows an antifungal activity, particularly, a strong antibacterial activity against pathogens of candidiasis, highly possibly shows a new antibacterial action different from those of existing antifungal agents, and further research and development in the future is expected (patent document 1). In addition, since the "kakeromycin" shows cytotoxicity to HepG2 liver cancer cell and PANC-1 pancreas cancer cell, its development as an anticancer agent is expected.

Therefore, a compound having a bicyclic oxaziridine ring which is a partial skeleton of kakeromycin can also be expected to show an antifungal activity and cytotoxicity.

DOCUMENT LIST

Patent Document

[patent document 1] WO2015/030197

SUMMARY OF THE INVENTION

Problems to be Solved by the Invention

An object of the present invention is to provide an oxaziridine compound, which shows an antifungal activity and cytotoxicity and is expected as a new antifungal agent or anticancer agent, and a production method thereof.

Means of Solving the Problems

The present inventors have conducted intensive studies in an attempt to solve the above-mentioned problem and found that an oxaziridine compound represented by the following formula 1, shows an antifungal activity and cytotoxicity, which resulted in the completion of the present invention.

Accordingly, the present invention provides the following. [1] A compound represented by the formula 1:

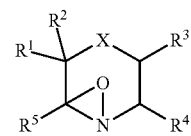

wherein
X is a single bond, —C(H)(R$^6$)— or —C(H)(R$^7$)—C(H)(R$^8$)—; and
R$^1$-R$^8$ are each independently a hydrogen atom, an optionally substituted hydrocarbon group or an optionally substituted heterocyclic group
(sometimes to be abbreviated as "compound 1" in the present specification) or a salt thereof;
[2] a production method of a compound represented by the formula 1:

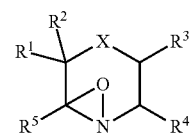

wherein
X is a single bond, —C(H)(R⁶)— or —C(H)(R⁷)—C(H)(R⁸)—; and R¹-R⁸ are each independently a hydrogen atom, an optionally substituted hydrocarbon group or an optionally substituted heterocyclic group,
or a salt thereof, which comprises a step of subjecting a compound represented by the formula 4:

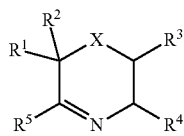

4 wherein X and R¹-R⁸ are as defined above (sometimes to be abbreviated as "compound 4" in the present specification) or a salt thereof to an oxidation reaction; [3] the production method of [2], further comprising a step of producing a compound represented by the formula 4 or a salt thereof by subjecting a compound represented by the formula 3:

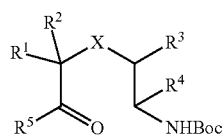

3 wherein X and R¹-R⁸ are as defined in [2] (sometimes to be abbreviated as "compound 3" in the present specification) or a salt thereof to a deprotection reaction;
[4] the production method of [3], further comprising a step of producing a compound represented by the formula 3 or a salt thereof by reacting a compound represented by the formula 2:

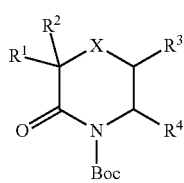

2 wherein X, R¹-R⁴ and R⁶-R⁸ are as defined in [2] (sometimes to be abbreviated as "compound 2" in the present specification) or a salt thereof with (A) a carbanion reagent represented by the formula: R⁵-M wherein M is MgX (X is a halogen atom), Li or Cu, when R⁵ is an optionally substituted hydrocarbon group or an optionally substituted heterocyclic group, or with (B) a hydride reagent when R⁵ is a hydrogen atom.

Effect of the Invention

According to the present invention, an oxaziridine compound, which shows an antifungal activity and cytotoxicity and is expected as a new antifungal agent or anticancer agent, and a production method thereof are provided.

DESCRIPTION OF EMBODIMENTS

The definitions of respective groups used in the structural formulas in the present specification are described in detail below.

X is a single bond, —O(H)(R⁶)— or —C(H)(R⁷)—C(H)(R⁸)—.

R¹-R⁸ are each independently a hydrogen atom, an optionally substituted hydrocarbon group or an optionally substituted heterocyclic group.

Examples of the "hydrocarbon group" of the "optionally substituted hydrocarbon group" include $C_{1-20}$ alkyl group, $C_{2-20}$ alkenyl group, $C_{2-20}$ alkynyl group, $C_{3-20}$ cycloalkyl group, $C_{3-20}$ cycloalkenyl group, $C_{6-20}$ aryl group, and $C_{7-20}$ aralkyl group.

Examples of the "$C_{1-20}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

Examples of the "$C_{2-20}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Examples of the "$C_{2-20}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl. The "$C_{2-20}$ alkynyl group" is preferably a "$C_{2-6}$ alkynyl group".

Examples of the "$C_{3-20}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl. The "$C_{3-20}$ cycloalkyl group" is preferably a "$C_{3-10}$ cycloalkyl group".

Examples of the "$C_{3-20}$ cycloalkenyl group" include cyclopropenyl, cyclobutenyl, cyclopentenyl, cyclohexenyl, cycloheptenyl, and cyclooctenyl.

Examples of the "$C_{6-20}$ aryl group" include phenyl, 1-naphthyl, 2-naphthyl, 1-anthryl, 2-anthryl, and 9-anthryl. The "$C_{6-20}$ aryl group" is preferably a "$C_{6-14}$ aryl group".

Examples of the "$C_{7-20}$ aralkyl group" include benzyl, phenethyl, naphthylmethyl, and phenylpropyl.

Examples of the "heterocyclic group" of the "optionally substituted heterocyclic group" include (i) aromatic heterocyclic group, (ii) nonaromatic heterocyclic group and (iii) 7- to 10-membered crosslinked heterocyclic group, each containing, as a ring-constituting atom besides carbon atom, 1 to 4 hetero atoms selected from nitrogen atom, sulfur atom and oxygen atom.

Examples of the "aromatic heterocyclic group" include a 5- to 14-membered (preferably 5- to 10-membered) aromatic heterocyclic group containing, as a ring-constituting atom besides carbon atom, 1 to 4 hetero atoms selected from nitrogen atom, sulfur atom and oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered condensed polycyclic (preferably di- or tricyclic) aromatic heterocyclic groups such as benzothiophenyl, benzofuranyl, benzimidazolyl, benzoxazolyl, benzoisooxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acrydinyl, phenazinyl, phenothiazinyl, phenoxazinyl and the like.

Examples of the "nonaromatic heterocyclic group" include a 3- to 14-membered (preferably 4- to 10-membered) nonaromatic heterocyclic group containing, as a ring-constituting atom besides carbon atom, 1 to 4 hetero atoms selected from nitrogen atom, sulfur atom and oxygen atom.

Preferable examples of the "nonaromatic heterocyclic group" include 3- to 8-membered monocyclic nonaromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered condensed polycyclic (preferably di- or tricyclic) nonaromatic heterocyclic groups such as dihydrobenzofuranyl, dihydrobenzoimidazolyl, dihydrobenzooxazolyl, dihydrobenzothiazolyl, dihydrobenzoisothiazolyl, dihydronaphto [2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

Preferable examples of the "7- to 10-membered cross-linked heterocyclic group" include quinuclidinyl, and 7-azabicyclo[2.2.1]heptanyl.

Examples of the "substituent" of the "optionally substituted hydrocarbon group" and "optionally substituted heterocyclic group" include the following:
(1) halogen atom,
(2) nitro group,
(3) cyano group,
(4) oxo group,
(5) hydroxy group,
(6) optionally substituted $C_{1-6}$ alkoxy group,
(7) optionally substituted $C_{6-14}$ aryloxy group,
(8) optionally substituted $C_{7-16}$ aralkyloxy group,
(9) optionally substituted aromatic heterocyclyl-oxy group,
(10) optionally substituted non-aromatic heterocyclyl-oxy group,
(11) optionally substituted $C_{1-6}$ alkyl-carbonyloxy group,
(12) optionally substituted $C_{6-14}$ aryl-carbonyloxy group,
(13) optionally substituted $C_{1-6}$ alkoxy-carbonyloxy group,
(14) optionally substituted mono- or di-$C_{1-6}$ alkyl-carbamoyloxy group,
(15) optionally substituted $C_{6-14}$ aryl-carbamoyloxy group,
(16) optionally substituted 5- to 14-membered aromatic heterocyclyl-carbonyloxy group,
(17) optionally substituted 3- to 14-membered non-aromatic heterocyclyl-carbonyloxy group,
(18) optionally substituted $C_{1-6}$ alkylsulfonyloxy group,
(19) optionally substituted $C_{6-14}$ arylsulfonyloxy group,
(20) optionally substituted $C_{1-6}$ alkylthio group,
(21) optionally substituted 5- to 14-membered aromatic heterocyclic group,
(22) optionally substituted 3- to 14-membered nonaromatic heterocyclic group,
(23) formyl group,
(24) carboxy group,
(25) optionally substituted $C_{1-6}$ alkyl-carbonyl group,
(26) optionally substituted $C_{6-14}$ aryl-carbonyl group,
(27) optionally substituted 5- to 14-membered aromatic heterocyclyl-carbonyl group,
(28) optionally substituted 3- to 14-membered non-aromatic heterocyclyl-carbonyl group,
(29) optionally substituted $C_{1-6}$ alkoxy-carbonyl group,
(30) optionally substituted $C_{6-14}$ aryloxy-carbonyl group,
(31) optionally substituted $C_{7-16}$ aralkyloxy-carbonyl group,
(32) carbamoyl group,
(33) thiocarbamoyl group,
(34) optionally substituted mono- or di-$C_{1-6}$ alkyl-carbamoyl group,
(35) optionally substituted $C_{6-14}$ aryl-carbamoyl group,
(36) optionally substituted 5- to 14-membered aromatic heterocyclyl-carbamoyl group,
(37) optionally substituted 3- to 14-membered non-aromatic heterocyclyl-carbamoyl group,
(38) optionally substituted $C_{1-6}$ alkylsulfonyl group,
(39) optionally substituted $C_{6-14}$ arylsulfonyl group,
(40) optionally substituted 5- to 14-membered aromatic heterocyclyl-sulfonyl group,
(41) optionally substituted $C_{1-6}$ alkylsulfinyl group,
(42) optionally substituted $C_{6-14}$ arylsulfinyl group,
(43) optionally substituted 5- to 14-membered aromatic heterocyclyl-sulfinyl group,
(44) amino group,
(45) optionally substituted mono- or di-$C_{1-6}$ alkylamino group,
(46) optionally substituted mono- or di-$C_{6-14}$ arylamino group,
(47) optionally substituted 5- to 14-membered aromatic heterocyclyl-amino group,
(48) optionally substituted $C_{7-16}$ aralkylamino group,
(49) formylamino group,
(50) optionally substituted $C_{1-6}$ alkyl-carbonylamino group,
(51) optionally substituted ($C_{1-6}$ alkyl)($C_{1-6}$ alkyl-carbonyl) amino group,
(52) optionally substituted $C_{6-14}$ aryl-carbonylamino group,
(53) optionally substituted $C_{1-6}$ alkoxy-carbonylamino group,
(54) optionally substituted $C_{7-16}$ aralkyloxy-carbonylamino group,
(55) optionally substituted $C_{1-6}$ alkylsulfonylamino group,
(56) optionally substituted $C_{6-14}$ arylsulfonylamino group,
(57) optionally substituted $C_{1-6}$ alkyl group,
(58) optionally substituted $C_{2-6}$ alkenyl group,
(59) optionally substituted $C_{2-6}$ alkynyl group,
(60) optionally substituted $C_{3-10}$ cycloalkyl group,
(61) optionally substituted $C_{3-10}$ cycloalkenyl group, and
(62) optionally substituted $C_{6-14}$ aryl group.

The number of the above-mentioned "substituent" of the "optionally substituted hydrocarbon group" and "optionally substituted heterocyclic group" is, for example, 1 to 5, preferably 1 to 3. When the number of the substituents is two or more, the respective substituents may be the same or different.

When X is —C(H)(R$^6$)—, R$^6$ is preferably hydrogen atom, optionally substituted $C_{2-6}$ alkynyl group, optionally substituted $C_{3-10}$ cycloalkyl group or optionally substituted $C_{6-14}$ aryl group, more preferably, a hydrogen atom, optionally substituted $C_{2-6}$ alkynyl group or optionally substituted $C_{6-14}$ aryl group, particularly preferably, hydrogen atom or optionally substituted $C_{6-14}$ aryl group.

When X is —C(H)(R$^7$)—C(H)(R$^8$)—, R$^7$ is preferably hydrogen atom, optionally substituted $C_{2-6}$ alkynyl group, optionally substituted $C_{3-10}$ cycloalkyl group or optionally substituted $C_{6-14}$ aryl group, more preferably, optionally substituted $C_{2-6}$ alkynyl group or optionally substituted $C_{6-14}$ aryl group, particularly preferably, optionally substituted $C_{6-14}$ aryl group, and R$^6$ is preferably hydrogen atom, optionally substituted $C_{2-6}$ alkynyl group, optionally substituted $C_{3-10}$ cycloalkyl group or optionally substituted $C_{6-14}$ aryl group, more preferably, optionally substituted $C_{2-6}$ alkynyl group or optionally substituted $C_{6-14}$ aryl group, particularly preferably, optionally substituted $C_{6-14}$ aryl group.

X is preferably —C(H)(R$^6$)— (R$^6$ is hydrogen atom, optionally substituted $C_{2-6}$ alkynyl group, optionally substituted $C_{3-10}$ cycloalkyl group or optionally substituted $C_{6-14}$ aryl group), more preferably, —C(H)(R$^6$)— (R$^6$ is hydrogen atom, optionally substituted $C_{2-6}$ alkynyl group or optionally substituted $C_{6-14}$ aryl group), particularly preferably, —C(H)(R$^6$)— (R$^6$ is hydrogen atom or optionally substituted $C_{6-14}$ aryl group).

R$^1$ is preferably hydrogen atom, optionally substituted $C_{2-6}$ alkynyl group, optionally substituted $C_{3-10}$ cycloalkyl group or optionally substituted $C_{6-14}$ aryl group, more preferably, hydrogen atom, optionally substituted $C_{2-6}$ alkynyl group or optionally substituted $C_{6-14}$ aryl group, particularly preferably, hydrogen atom or optionally substituted $C_{6-14}$ aryl group.

R$^2$ is preferably hydrogen atom, optionally substituted $C_{2-6}$ alkynyl group, optionally substituted $C_{3-10}$ cycloalkyl group or optionally substituted $C_{6-14}$ aryl group, more preferably, hydrogen atom, optionally substituted $C_{2-6}$ alkynyl group or optionally substituted $C_{6-14}$ aryl group, particularly preferably, hydrogen atom or optionally substituted $C_{6-14}$ aryl group.

R$^3$ is preferably hydrogen atom, optionally substituted $C_{2-6}$ alkynyl group, optionally substituted $C_{3-10}$ cycloalkyl group or optionally substituted $C_{6-14}$ aryl group, more preferably, hydrogen atom, optionally substituted $C_{2-6}$ alkynyl group or optionally substituted $C_{6-14}$ aryl group, particularly preferably, hydrogen atom or optionally substituted $C_{6-14}$ aryl group.

R$^4$ is preferably hydrogen atom, optionally substituted $C_{2-6}$ alkynyl group, optionally substituted $C_{3-10}$ cycloalkyl group or optionally substituted $C_{6-14}$ aryl group, more preferably, hydrogen atom, optionally substituted $C_{2-6}$ alkynyl group or optionally substituted $C_{6-14}$ aryl group, particularly preferably, hydrogen atom or optionally substituted $C_{6-14}$ aryl group.

R$^5$ is preferably hydrogen atom, optionally substituted $C_{2-6}$ alkynyl group, optionally substituted $C_{3-10}$ cycloalkyl group or optionally substituted $C_{6-14}$ aryl group (e.g., phenyl), more preferably, optionally substituted $C_{2-6}$ alkynyl group or optionally substituted $C_{6-14}$ aryl group (e.g., phenyl), particularly preferably, optionally substituted $C_{6-14}$ aryl group (e.g., phenyl).

Preferable examples of compound 1 include the following compounds.

[Compound 1-1]
Compound 1 wherein
X is —C(H)(R$^6$)— (R$^6$ is hydrogen atom, optionally substituted $C_{2-6}$ alkynyl group, optionally substituted $C_{3-10}$ cycloalkyl group or optionally substituted $C_{6-14}$ aryl group);

R$^1$ is hydrogen atom, optionally substituted $C_{2-6}$ alkynyl group, optionally substituted $C_{3-10}$ cycloalkyl group or optionally substituted $C_{6-14}$ aryl group;

R$^2$ is hydrogen atom, optionally substituted $C_{2-6}$ alkynyl group, optionally substituted $C_{3-10}$ cycloalkyl group or optionally substituted $C_{6-14}$ aryl group;

R$^3$ is hydrogen atom, optionally substituted $C_{2-6}$ alkynyl group, optionally substituted $C_{3-10}$ cycloalkyl group or optionally substituted $C_{6-14}$ aryl group;

R$^4$ is hydrogen atom, optionally substituted $C_{2-6}$ alkynyl group, optionally substituted $C_{3-10}$ cycloalkyl group or optionally substituted $C_{6-14}$ aryl group; and R$^5$ is hydrogen atom, optionally substituted $C_{2-6}$ alkynyl group, optionally substituted $C_{3-10}$ cycloalkyl group or optionally substituted $C_{6-14}$ aryl group (e.g., phenyl).

[Compound 1-2]
Compound 1 wherein
X is —C(H)(R$^6$)— (R$^6$ is hydrogen atom, optionally substituted $C_{2-6}$ alkynyl group or optionally substituted $C_{6-14}$ aryl group);

R$^1$ is hydrogen atom, optionally substituted $C_{2-6}$ alkynyl group or optionally substituted $C_{6-14}$ aryl group;

R$^2$ is hydrogen atom, optionally substituted $C_{2-6}$ alkynyl group or optionally substituted $C_{6-14}$ aryl group;

R$^3$ is hydrogen atom, optionally substituted $C_{2-6}$ alkynyl group or optionally substituted $C_{6-14}$ aryl group;

R$^4$ is hydrogen atom, optionally substituted $C_{2-6}$ alkynyl group or optionally substituted $C_{6-14}$ aryl group; and R$^5$ is optionally substituted $C_{2-6}$ alkynyl group or optionally substituted $C_{6-14}$ aryl group (e.g., phenyl).

[Compound 1-3]
Compound 1 wherein
X is —C(H)(R$^6$)— (R$^6$ is hydrogen atom or optionally substituted $C_{6-14}$ aryl group);

R$^1$ is hydrogen atom or optionally substituted $C_{6-14}$ aryl group;

R$^2$ is hydrogen atom or optionally substituted $C_{6-14}$ aryl group;

R$^3$ is hydrogen atom or optionally substituted $C_{6-14}$ aryl group;

R$^4$ is hydrogen atom or optionally substituted $C_{6-14}$ aryl group; and

R$^5$ is optionally substituted $C_{6-14}$ aryl group (e.g., phenyl).

The production method of the oxaziridine compound of the present invention is explained below.

The whole scheme of the production method of the oxaziridine compound of the present invention is shown below.

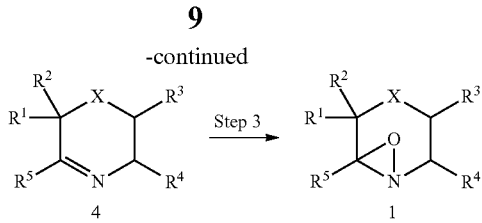

wherein each symbol is as defined above.

The production method of the oxaziridine compound 1 or a salt thereof of the present invention is characterized in that it includes a step of subjecting compound 4 or a salt thereof to an oxidation reaction (step 3).

The production method of the oxaziridine compound 1 or a salt thereof of the present invention may further include a step of producing compound 4 or a salt thereof by subjecting compound 3 or a salt thereof to a deprotection reaction (step 2).

The production method of the oxaziridine compound 1 or a salt thereof of the present invention may further include a step of producing compound 3 or a salt thereof by reacting compound 2 or a salt thereof with a carbanion reagent or a hydride reagent (step 1).

(Step 1: Production of N-Boc-aminoketone (3))

N-Boc-aminoketone (3) can be synthesized by a treatment of N-Boc-lactam (2) with (A) a carbanion reagent when $R^5$ is an optionally substituted hydrocarbon group or an optionally substituted heterocyclic group, or with (B) a hydride reagent when $R^5$ is a hydrogen atom. Examples of the carbanion reagent include a carbanion reagent represented by the formula: $R^5$-M wherein M is MgX (X is a halogen atom), Li or Cu, that is, organic magnesium compounds such as Grignard reagent and the like, organic lithium compound, organic copper compound and the like, and particularly, organic magnesium compounds such as Grignard reagent and the like are preferable. Examples of the hydride reagent include diisobutylaluminum hydride, $NaBH_4$, $LiAlH_4$ and the like, and particularly, diisobutylaluminum hydride is preferable. The carbanion reagent can be used at generally 1-3 molar equivalents, preferably 1-1.5 molar equivalents, relative to N-Boc-lactam (2). The hydride reagent can be used at generally 0.5-3 molar equivalents, preferably 1-1.5 molar equivalents, relative to N-Boc-lactam (2). The reaction temperature is generally −78° C.-30° C., preferably −78° C.-0° C. While the reaction time varies depending on the kind of the reagents, reaction temperature and the like, it is generally 0.5-48 hr, preferably 0.5-3 hr. As the reaction solvent, THF, diethyl ether, hexane, toluene, or a mixed solvent thereof and the like can be used, and particularly, THF solvent is preferable.

N-Boc-lactam (2) may be a commercially available product, and can also be produced according to a method known per se or a method analogous thereto.

(Step 2: Production of Cyclic Imine (4))

Cyclic imine (4) can be synthesized by removing a Boc protecting group of the amino group of N-Boc-aminoketone (3). As the deprotecting agent, trifluoroacetic acid, hydrochloric acid, sodium hydroxide, potassium hydroxide and the like can be used at generally 1-50 molar equivalents, preferably 1-10 molar equivalents, relative to N-Boc-aminoketone (3), and particularly, trifluoroacetic acid is preferable. The reaction temperature is generally 0-50° C., preferably 20-30° C. While the reaction time varies depending on the kind of the reagents, reaction temperature and the like, it is generally 1-24 hr, preferably 1-3 hr. As the reaction solvent, THF, ethyl acetate, dichloromethane, dichloroethane, or a mixed solvent thereof and the like can be used, and particularly, dichloromethane and dichloroethane are preferable.

(Step 3: Production of Bicyclic Oxaziridine (1))

Bicyclic oxaziridine (1) can be synthesized by an oxidation reaction of cyclic imine (4). As the oxidant, m-chloroperbenzoic acid, peracetic acid and the like can be used at generally 1-5 molar equivalents, preferably 1-2 molar equivalents, relative to cyclic imine (4), and particularly, m-chloroperbenzoic acid is preferable. The reaction temperature is generally 0-50° C., preferably 10-30° C. While the reaction time varies depending on the kind of the reagents, reaction temperature and the like, it is generally 0.5-12 hr, preferably 1-2 hr. As the reaction solvent, THF, ethyl acetate, dichloromethane, dichloroethane, toluene, ethanol, methanol, acetonitrile, or a mixed solvent thereof and the like can be used, and particularly, THF, methanol and dichloromethane are preferable.

The bicyclic oxaziridine and a synthetic intermediate thereof of the present invention may be salts. Examples of such salt include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like. Of these salts, a pharmaceutically acceptable salt is preferable.

The bicyclic oxaziridine and a salt thereof of the present invention have a strong antifungal activity against a broad range of fungi, and are expected to be new antifungal agents. In addition, the bicyclic oxaziridine and a salt thereof show cytotoxicity against cancer cells, and are expected as new anticancer agents. Therefore, the bicyclic oxaziridine and a salt thereof can be used as an active ingredient of medicaments, pesticides and the like.

Examples of the fungi to be the target of the antifungal agent include, but are not limited to, fungi such as the genus *Candida* (e.g., *Candida albicans, Candida parapsilosis, Candida tropicalis, Candida krusei, Candida glabrata, Candida quilliermondii, Candida lusitaniae* etc.), the genus *Aspergillus* (e.g., *Aspergillus fumigatus, Aspergillus flavus, Aspergillus niger, Aspergillus terreus* etc.), the genus *Trichophyton* (e.g., *Trichophyton rubrum, Trichophyton mentagrophytes, Trichophyton tonsurans, Microsporum canis, Microsporum gypseum, Trichophyton verrucosum* etc.) and the like. Mycosis is not particularly limited, and deep skin mycosis, deep mycosis, mycetoma, and fungemia can be mentioned.

When the antifungal agent is used as a pesticide, the target crop is not particularly limited and, for example, plants such as grain (e.g., rice, barley, wheat, rye, oats, corn, kaoliang etc.), beans (soybean, adzuki bean, broad bean, pea, peanut etc.), fruit-tree, fruits (apple, citrus, pear, grapes, peach, ume (Japanese plum), cherry, walnut, almond, banana, strawberry etc.), vegetables (cabbage, tomato, spinach, broccoli, lettuce, onion, green onion, bell pepper etc.), root vegetables (carrot, potato, sweet potato, radish, lotus root, turnip etc.), crops for processing (cotton, hemp, kozo (paper mulberry), mitsumata plant, rape seed, beet, hop, sugarcane, sugar beet, olive, rubber, coffee, tobacco, tea etc.), gourds (pumpkin, cucumber, watermelon, melon etc.), grasses (orchard grass, sorghum, timothy, clover, alfalfa etc.), sods (Korean lawn grass, bentgrass etc.), crops for flavor etc. (lavender, rosemary, thyme, parsley, pepper, ginger etc.), flowering plants (chrysanthemum, rose, orchid etc.) and the like can be mentioned. The antifungal agent can be used for controlling the diseases related to the aforementioned fungi in the crops, by treating the target crop and/or seed of the target crop with an effective amount thereof.

The pesticide can be used in the following form, and generally used together with an adjuvant conventionally used in the pharmaceutical fields. The bicyclic oxaziridine and a salt thereof of the present invention are formulated by a known method into, for example, emulsion stock solution, sprayable paste, sprayable or dilutable solution, dilutable emulsion, wettable agent, water soluble powder, powder, granule, flowable pesticide, dry flowable pesticide, smoking agent, fumigant and, for example, capsule made of a polymer substance.

As additive and carrier when the object is a solid agent, plant-derived powder such as soy flour, wheat flour and the like, mineral fine powder such as diatomaceous earth, apatite, plaster, talc, bentonite, clay and the like, and organic and inorganic compounds such as sodium benzoate, urea, salt cake and the like can be used.

When a liquid dosage form is desired, aromatic hydrocarbons such as vegetable oil, mineral oil, kerosene, xylene and toluene, amides such as formamide, and dimethylformamide, sulfoxides such as dimethyl sulfoxide, ketones such as methyl isobutyl ketone and acetone, trichloroethylene, water and the like are used as solvents. To afford these preparations in a uniform and stable form, a surfactant can also be added where necessary. The thus-obtained wettable agent, emulsion, aqueous solution, flowable pesticide, and dry flowable pesticide are diluted with water to a given concentration and used as a suspension or emulsion, and powder and granule are used by directly spraying on the soil or plant.

The content and dose of the active ingredient in a pesticide containing the bicyclic oxaziridine and a salt thereof of the present invention can be changed in a wide range depending on the dosage form, the kind of fungi to be the application target, target crop and the like.

On the other hand, when the antifungal agent is used as a medicament, it can be administered to a treatment target, for example, a mammal (e.g., human, mouse, rat, hamster, rabbit, cat, dog, bovine, sheep, monkey etc.) by an oral or parenteral administration route (e.g., intravenous injection, intramuscular injection, subcutaneous administration, rectal administration, transdermal administration).

When the antifungal agent is transdermally administered, it can contain, besides the above-mentioned active ingredient, oily base, emulsifier and emulsion stabilizer, solubilizing agents, powder component, polymer component, adhesiveness improver, film-forming agent, pH adjuster, antioxidant, antiseptic agent, preservative, shape retention agent, moisturizer, skin protector, algefacient, flavor, colorant, chelating agent, lubricant, blood circulation promoter, astringent, tissue repair promoter, adiaphoretic, plant extraction component, animal extraction component, anti-inflammatory agent, antipruritic agent and the like as necessary. As these additives, those generally used for preparations can be used.

The antifungal agent can be used by formulating the above-mentioned components other than the active ingredient and the like into external drugs such as cream, liquid, lotion, emulsion, tincture, ointment, aqueous gel, oily gel, aerosol, powder, shampoo, soap, enamel agent for application to nail and the like, by a method conventionally used in the field of pharmaceutical preparations.

When the antifungal agent is orally administered, it can be prepared into a dosage form suitable for oral administration such as capsule, tablet, granule, powder, pill, fine granules, troche and the like. These preparations can be produced using additives generally used for oral preparations, such as excipient, filler, binder, moistening agent, disintegrant, surfactant, lubricant, dispersing agent, buffering agent, preservative, solubilizing agent, antiseptic agent, flavoring agent, soothing agent, stabilizer and the like by a conventional method.

Examples of the cells to be the target of the anticancer agent include, but are not limited to, cancer cells such as HepG2 cell (liver cancer cell), $PANC_1$ cell (pancreas cancer cell) and the like. The cancer is not particularly limited, and brain tumor, skin cancer, leukemia, esophagus cancer, gastric cancer, colorectal cancer, breast cancer, prostate cancer, rectal cancer, osteosarcoma and the like can be mentioned.

EXAMPLES

The present invention is explained in more detail by referring to the following Examples. These do not limit the present invention, and may be changed within the scope of the present invention.

$^1$H NMR spectrum was measured by a nuclear magnetic resonance apparatus (manufactured by Varian, 400 MR), and all δ values are shown in ppm. Mass spectrum was measured by HPLC-Chip/QTOF mass spectrometry system (Agilent Technologies), and m/z values are shown.

Example 1

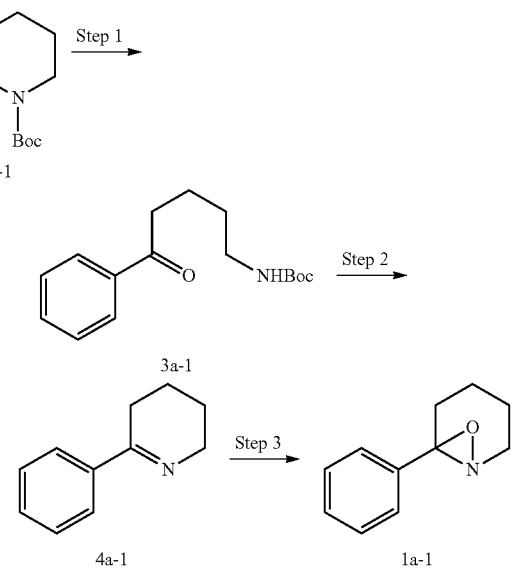

(Step 1)

N-Boc-lactam 2a-1 (300 mg, 1.50 mmol) was dissolved in THF (3 mL), a THF solution of phenylmagnesium bromide (1 mol/L solution, 1.5 mL, 1.50 mmol) was added at 0° C., and the mixture was stirred at 0° C. for 1 hr. Water (1.0 mL) was added, anhydrous sodium sulfate was added, water in the reaction system was removed, and the mixture was filtered through cotton. The obtained filtrate was concentrated by a rotary evaporator. The obtained crude product was purified by silica gel column chromatography (solvent: hexane and ethyl acetate) to give N-Boc-aminoketone 3a-1 (313 mg, 1.13 mmol) as a colorless liquid (yield 75%).

MS: m/z 278 ([M+1], $C_{16}H_{23}NO_3$)

(Step 2)

N-Boc-aminoketone 3a-1 (50 mg, 0.18 mmol) was dissolved in dichloroethane (3 mL), trifluoroacetic acid (0.5 mL) was added, and the mixture was stirred at room temperature for 1 hr. The reaction mixture was concentrated by a rotary evaporator to give cyclic imine 4a-1 (26 mg, 0.16 mmol) as a colorless liquid (yield 90%).

MS: m/z 160 ([M+1], $C_{11}H_{13}N$)

(Step 3)

Cyclic imine 4a-1 (10 mg, 0.06 mmol) was dissolved in THF (3 mL), m-chloroperbenzoic acid (11 mg) was added, and the mixture was stirred at room temperature for 3 hr and concentrated by a rotary evaporator. The obtained crude product was purified by silica gel column chromatography (solvent: hexane and ethyl acetate) to give bicyclic oxaziridine 1a-1 (3 mg, 0.018 mmol) as a yellow liquid (yield 30%).

$^1$H NMR: δ 1.80-2.26 (m, 4H), 2.32-2.76 (m, 2H), 2.90-3.28 (m, 2H), 7.10-7.50 (m, 5H); MS: m/z 176 ([M+1], $C_{11}H_{13}NO$)

INDUSTRIAL APPLICABILITY

According to the present invention, an oxaziridine compound showing an antifungal activity and cytotoxicity and expected as a new antifungal agent or anticancer agent, and a is production method thereof are provided.

The invention claimed is:

1. A compound represented by the formula 1:

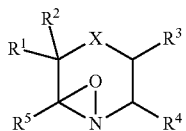

wherein

X is —C(H)($R^6$)— or —C(H)($R^7$)—C(H)($R^8$)—;

$R^1$, $R^2$, $R^3$, $R^4$, $R^6$, $R^7$, and $R^8$ are each independently a hydrogen atom, an optionally substituted hydrocarbon group selected from $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl, and $C_{7-20}$ aralkyl, or an optionally substituted heterocyclic group selected from (i) aromatic heterocyclic groups, (ii) nonaromatic heterocyclic groups, and (iii) 7- to 10-membered crosslinked heterocyclic groups, each containing, as a ring-constituting atom besides carbon atoms, 1 to 4 hetero atoms independently selected from nitrogen, sulfur, and oxygen, and $R^5$ is a hydrogen atom, $C_{1-20}$ alkyl substituted with 1 to 5 substituents independently selected from halo, nitro, cyano, oxo, hydroxy, $C_{1-6}$ alkoxy, $C_{6-14}$ aryloxy, $C_{7-16}$ aralkyloxy, aromatic heterocyclyl-oxy, non-aromatic heterocyclyl-oxy, $C_{1-6}$ alkyl-carbonyloxy, $C_{6-14}$ aryl-carbonyloxy, $C_{1-6}$ alkoxy-carbonyloxy, mono- or di-$C_{1-6}$ alkyl-carbamoyloxy, $C_{6-14}$ aryl-carbamoyloxy, 5- to 14-membered aromatic heterocyclyl-carbonyloxy, 3- to 14-membered non-aromatic heterocyclyl-carbonyloxy, $C_{1-6}$ alkylsulfonyloxy, $C_{6-14}$ arylsulfonyloxy, $C_{1-6}$ alkylthio, 5- to 14-membered aromatic heterocyclyl, 3- to 14-membered nonaromatic heterocyclyl, formyl, carboxy, $C_{1-6}$ alkyl-carbonyl, $C_{6-14}$ aryl-carbonyl, 5- to 14-membered aromatic heterocyclyl-carbonyl, 3- to 14-membered non-aromatic heterocyclyl-carbonyl, $C_{1-6}$ alkoxy-carbonyl, $C_{6-14}$ aryloxy-carbonyl, $C_{7-16}$ aralkyloxy-carbonyl, carbamoyl, thiocarbamoyl, mono- or di-$C_{1-6}$ alkyl-carbamoyl, $C_{6-14}$ aryl-carbamoyl, 5- to 14-membered aromatic heterocyclyl-carbamoyl, 3- to 14-membered non-aromatic heterocyclyl-carbamoyl, $C_{1-6}$ alkylsulfonyl, $C_{6-14}$ arylsulfonyl, 5- to 14-membered aromatic heterocyclyl-sulfonyl, $C_{1-6}$ alkylsulfinyl, $C_{6-14}$ arylsulfinyl, 5- to 14-membered aromatic heterocyclyl-sulfinyl, amino, mono- or di-$C_{1-6}$ alkylamino, mono- or di-$C_{6-14}$ arylamino, 5- to 14-membered aromatic heterocyclyl-amino, $C_{7-16}$ aralkylamino, formylamino, $C_{1-6}$ alkyl-carbonylamino, ($C_{1-6}$ alkyl)($C_{1-6}$ alkyl-carbonyl)amino, $C_{6-14}$ aryl-carbonylamino, $C_{1-6}$ alkoxy-carbonylamino, $C_{7-16}$ aralkyloxy-carbonylamino, $C_{1-6}$ alkylsulfonylamino, $C_{6-14}$ arylsulfonylamino, $C_{1-6}$ alkyl, $C_{2-6}$ alkenyl, $C_{2-6}$ alkynyl, $C_{3-10}$ cycloalkyl, $C_{3-10}$ cycloalkenyl, and $C_{6-14}$ aryl, an optionally substituted hydrocarbon group selected from $C_{2-20}$ alkenyl, $C_{2-20}$ alkynyl, $C_{3-20}$ cycloalkyl, $C_{3-20}$ cycloalkenyl, $C_{6-20}$ aryl, and $C_{7-20}$ aralkyl, or an optionally substituted heterocyclic group selected from (i) aromatic heterocyclic groups, (ii) nonaromatic heterocyclic groups, and (iii) 7- to 10-membered crosslinked heterocyclic groups, each containing, as a ring-constituting atom besides carbon atoms, 1 to 4 hetero atoms independently selected from nitrogen, sulfur, and oxygen, wherein a substituted hydrocarbon group and/or substituted heterocyclic group is substituted with 1 to 5 substituents independently selected from halo, nitro, cyano, oxo, hydroxy, $C_{1-6}$ alkoxy, $C_{6-14}$ aryloxy, $C_{7-16}$ aralkyloxy, aromatic heterocyclyl-oxy, non-aromatic heterocyclyl-oxy, $C_{1-6}$ alkyl-carbonyloxy, $C_{6-14}$ aryl-carbonyloxy, $C_{1-6}$ alkoxy-carbonyloxy, mono- or di-$C_{1-6}$ alkyl-carbamoyloxy, $C_{6-14}$ aryl-carbamoyloxy, 5- to 14-membered aromatic heterocyclyl-carbonyloxy, 3- to 14-membered non-aromatic heterocyclyl-carbonyloxy, $C_{1-6}$ alkylsulfonyloxy, $C_{6-14}$ arylsulfonyloxy, $C_{1-6}$ alkylthio, 5- to 14-membered aromatic heterocyclyl, 3- to 14-membered nonaromatic heterocyclyl, formyl, carboxy, $C_{1-6}$ alkyl-carbonyl, $C_{6-14}$ aryl-carbonyl, 5- to 14-membered aromatic heterocyclyl-carbonyl, 3- to 14-membered non-aromatic heterocyclyl-carbonyl, $C_{1-6}$ alkoxy-carbonyl, $C_{6-14}$ aryloxy-carbonyl, $C_{7-16}$ aralkyloxy-carbonyl, carbamoyl, thiocarbamoyl, mono- or di-$C_{1-6}$ alkyl-carbamoyl, $C_{6-14}$ aryl-carbamoyl, 5- to 14-membered aromatic heterocyclyl-carbamoyl, 3- to 14-membered non-aromatic heterocyclyl-carbamoyl, $C_{1-6}$ alkylsulfonyl, $C_{6-14}$ arylsulfonyl, 5- to 14-membered aromatic heterocyclyl-sulfonyl, $C_{1-6}$ alkylsulfinyl, $C_{6-14}$ arylsulfinyl, 5- to 14-membered aromatic heterocyclyl-sulfinyl, amino, mono- or di-$C_{1-6}$ alkylamino, mono- or di-$C_{6-14}$ arylamino, 5- to 14-membered aromatic heterocyclyl-amino, $C_{7-16}$ aralkylamino, formylamino, $C_{1-6}$ alkyl-carbonylamino, ($C_{1-6}$ alkyl)($C_{1-6}$ alkyl-carbonyl)amino, $C_{6-14}$ aryl-carbonylamino, $C_{1-6}$ alkoxy-carbonylamino, $C_{7-16}$ aralkyloxy-carbonylamino, $C_{1-6}$ alkylsulfonylamino, $C_{6-14}$ arylsulfonylamino, $C_{1-6}$ alkyl, $C_{2-6}$ alkenyl, $C_{2-6}$ alkynyl, $C_{3-10}$ cycloalkyl, $C_{3-10}$ cycloalkenyl, and $C_{6-14}$ aryl, or a salt thereof.

2. A production method of a compound represented by the formula 1:

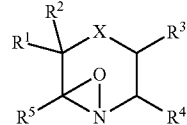

wherein
X is a single bond, —C(H)(R$^6$)— or —C(H)(R$^7$)—C(H)(R$^8$)—; and
R$^1$-R$^8$ are each independently
a hydrogen atom,
an optionally substituted hydrocarbon group selected from C$_{1-20}$ alkyl, C$_{2-20}$ alkenyl, C$_{2-20}$ alkynyl, C$_{3-20}$ cycloalkyl, C$_{3-20}$ cycloalkenyl, C$_{6-20}$ aryl, and C$_{7-20}$ aralkyl, or
an optionally substituted heterocyclic group selected from (i) aromatic heterocyclic groups, (ii) nonaromatic heterocyclic groups, and (iii) 7- to 10-membered crosslinked heterocyclic groups, each containing, as a ring-constituting atom besides carbon atoms, 1 to 4 hetero atoms independently selected from nitrogen, sulfur, and oxygen, and
a substituted hydrocarbon group and/or substituted heterocyclic group is substituted with 1 to 5 substituents independently selected from halo, nitro, cyano, oxo, hydroxy, C$_{1-6}$ alkoxy, C$_{6-14}$ aryloxy, C$_{7-16}$ aralkyloxy, aromatic heterocyclyl-oxy, nonaromatic heterocyclyl-oxy, C$_{1-6}$ alkyl-carbonyloxy, C$_{6-14}$ aryl-carbonyloxy, C$_{1-6}$ alkoxy-carbonyloxy, mono- or di-C$_{1-6}$ alkyl-carbamoyloxy, C$_{6-14}$ aryl-carbamoyloxy, 5- to 14-membered aromatic heterocyclyl-carbonyloxy, 3- to 14-membered non-aromatic heterocyclyl-carbonyloxy, C$_{1-6}$ alkylsulfonyloxy, C$_{6-14}$ arylsulfonyloxy, C$_{1-6}$ alkylthio, 5- to 14-membered aromatic heterocyclyl, 3- to 14-membered nonaromatic heterocyclyl, formyl, carboxy, C$_{1-6}$ alkyl-carbonyl, C$_{6-14}$ aryl-carbonyl, 5- to 14-membered aromatic heterocyclyl-carbonyl, 3- to 14-membered non-aromatic heterocyclyl-carbonyl, C$_{1-6}$ alkoxy-carbonyl, C$_{6-14}$ aryloxy-carbonyl, C$_{7-16}$ aralkyloxy-carbonyl, carbamoyl, thiocarbamoyl, mono- or di-C$_{1-6}$ alkyl-carbamoyl, C$_{6-14}$ aryl-carbamoyl, 5- to 14-membered aromatic heterocyclyl-carbamoyl, 3- to 14-membered non-aromatic heterocyclyl-carbamoyl, C$_{1-6}$ alkylsulfonyl, C$_{6-14}$ arylsulfonyl, 5- to 14-membered aromatic heterocyclyl-sulfonyl, C$_{1-6}$ alkylsulfinyl, C$_{6-14}$ arylsulfinyl, 5- to 14-membered aromatic heterocyclyl-sulfinyl, amino, mono- or di-C$_{1-6}$ alkylamino, mono- or di-C$_{6-14}$ arylamino, 5- to 14-membered aromatic heterocyclyl-amino, C$_{7-16}$ aralkylamino, formylamino, C$_{1-6}$ alkyl-carbonylamino, (C$_{1-6}$ alkyl)(C$_{1-6}$ alkyl-carbonyl)amino, C$_{6-14}$ aryl-carbonylamino, C$_{1-6}$ alkoxy-carbonylamino, C$_{7-16}$ aralkyloxy-carbonylamino, C$_{1-6}$ alkylsulfonylamino, C$_{6-14}$ arylsulfonylamino, C$_{1-6}$ alkyl, C$_{2-6}$ alkenyl, C$_{2-6}$ alkynyl, C$_{3-10}$ cycloalkyl, C$_{3-10}$ cycloalkenyl, and C$_{6-14}$ aryl,
or a salt thereof, which comprises reacting a compound represented by the formula 4:

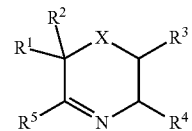

wherein X and R$^1$-R$^8$ are as defined above,
or a salt thereof, with an oxidant to form a compound represented by the formula 1.

3. The production method according to claim 2, further comprising producing the compound represented by the formula 4 or a salt thereof by deprotecting a compound represented by the formula 3:

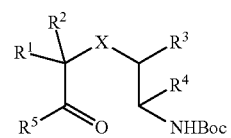

wherein X and R$^1$-R$^8$ are as defined in claim 2,
or a salt thereof, in the presence of an acid or base to remove the t-butyloxycarbonyl (Boc) protecting group to form the compound represented by the formula 4.

4. The production method according to claim 3, further comprising a step of producing the compound represented by the formula 3 or a salt thereof by reacting a compound represented by the formula 2:

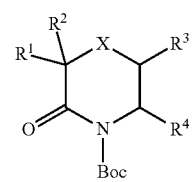

wherein X, R$^1$-R$^4$ and R$^6$-R$^8$ are as defined in claim 2,
or a salt thereof with
(A) a carbanion reagent represented by the formula: R$^5$-M wherein M is MgX, Li or Cu, and X is a halogen atom, when R$^5$ is an optionally substituted hydrocarbon group or an optionally substituted heterocyclic group, or
(B) a hydride reagent when R$^5$ is a hydrogen atom
to form the compound represented by the formula 3.

5. The production method according to claim 2, wherein the oxidant is m-chloroperbenzoic acid or peracetic acid.

6. The production method according to claim 5, wherein reacting the compound represented by the formula 4 or a salt thereof with an oxidant takes place at a temperature from 0-50° C.

7. The production method according to claim 2, wherein reacting the compound represented by the formula 4 or a salt thereof with an oxidant takes place at a temperature from 0-50° C.

8. The production method according to claim 3, wherein the acid is trifluoroacetic acid or hydrochloric acid or the base is sodium hydroxide or potassium hydroxide.

9. The production method according to claim 8, wherein the deprotecting takes place at a temperature from 0-50° C.

10. The production method according to claim 3, wherein the deprotecting takes place at a temperature from 0-50° C.

* * * * *